United States Patent
Yee et al.

(10) Patent No.: US 6,648,913 B1
(45) Date of Patent: Nov. 18, 2003

(54) GUIDEWIRE-ACCESS MODULAR INTRALUMINAL PROSTHESIS WITH CONNECTING SECTION

(75) Inventors: Carl E. Yee, Austin, TX (US); José F. Nuñez, St. Anthony, MN (US); Marianne W. Staudenmeier, North Haledon, NJ (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/327,069

(22) Filed: Jun. 7, 1999

(51) Int. Cl.[7] .................................................. A61F 2/06
(52) U.S. Cl. ..................................... 623/1.35; 623/1.16
(58) Field of Search .............................. 623/1.13, 1.15, 623/1.16, 1.18, 1.2, 1.23, 1.31, 1.34, 1.35, 1.44

(56) References Cited

U.S. PATENT DOCUMENTS

| | | |
|---|---|---|
| 3,657,744 A | 4/1972 | Ersek |
| 4,140,126 A | 2/1979 | Choudhury |
| 4,562,596 A | 1/1986 | Kornberg |
| 4,577,631 A | 3/1986 | Kreamer |
| 4,733,665 A | 3/1988 | Palmaz |
| 4,787,899 A | 11/1988 | Lazarus |
| 5,078,726 A | 1/1992 | Kreamer |
| 5,104,399 A | 4/1992 | Lazarus |
| 5,219,355 A | 6/1993 | Parodi et al. |
| 5,360,443 A | 11/1994 | Barone et al. |
| 5,522,880 A | 6/1996 | Barone et al. |
| 5,562,724 A | 10/1996 | Vorwerk et al. |
| 5,571,171 A | 11/1996 | Barone et al. |
| 5,571,173 A | 11/1996 | Parodi |
| 5,575,817 A | 11/1996 | Martin |

(List continued on next page.)

FOREIGN PATENT DOCUMENTS

| | | |
|---|---|---|
| EP | 0 508 473 A2 | 4/1992 |
| EP | 0 539 237 A1 | 10/1992 |
| EP | 1 029 518 | 8/2000 |
| WO | WO 98/06355 | 2/1998 |
| WO | 98/32399 | 7/1998 |

OTHER PUBLICATIONS

U. S. patent application Ser. No. 08/822,858, to Parodi, filed Mar. 24, 1997.

*Primary Examiner*—Bruce Snow
*Assistant Examiner*—Brian E Pellegrino
(74) *Attorney, Agent, or Firm*—RatnerPrestia

(57) ABSTRACT

A multi-component intraluminal prosthesis is adapted for insertion into and in vivo assembly within a body lumen to repair the lumen, the components including secure and/or fluid-tight mating sections. The prosthesis comprises a female mating member comprising a main body portion, a funnel-shaped end, and a sealing segment connecting the main body portion to the funnel-shaped end; and a male mating member adapted for in vivo assembly with the sealing segment of the female mating member. The sealing segment may be essentially cylindrical or it may taper with decreasing diameter from the main body to the funnel-shaped end. The sealing segment and adjacent funnel-shaped end may together form an hourglass-shaped end. A biocompatible graft material may cover the inner surface of the funnel-shaped end. To secure a fluid-tight seal, the outer surface of the male member and the inner surface of the female member are covered with a biocompatible graft material in their respective mating segments. The prosthesis may form a bifurcated intraluminal prosthesis adapted, for example, for deployment in the infra-renal aorta and the iliac arteries, where the main body component forms the main aortic body, the integral first leg member forms the first iliac segment, and the second leg member forms the second iliac segment.

16 Claims, 2 Drawing Sheets

U.S. PATENT DOCUMENTS

| | | |
|---|---|---|
| 5,578,071 A | 11/1996 | Parodi |
| 5,578,072 A | 11/1996 | Barone et al. |
| 5,591,229 A | 1/1997 | Parodi |
| 5,609,627 A | 3/1997 | Goicoechea et al. |
| 5,628,788 A | 5/1997 | Pinchuk |
| 5,632,763 A | 5/1997 | Glastra |
| 5,632,772 A | 5/1997 | Alcime et al. |
| 5,639,278 A | 6/1997 | Dereume et al. |
| 5,683,449 A | 11/1997 | Marcade .................... 623/1.35 |
| 5,824,037 A | 10/1998 | Fogarty et al. |
| 5,824,040 A | 10/1998 | Cox et al. |
| 5,824,042 A | 10/1998 | Lombardi et al. |
| 5,984,955 A | 11/1999 | Wisselink |
| 5,993,481 A * | 11/1999 | Marcade et al. ............. 623/1.3 |
| 6,015,431 A | 1/2000 | Thornton et al. |
| 6,030,415 A | 2/2000 | Chuter |
| 6,099,558 A * | 8/2000 | White et al. ............... 623/1.13 |
| 6,302,908 B1 * | 10/2001 | Parodi ...................... 623/1.31 |

* cited by examiner

GUIDEWIRE-ACCESS MODULAR INTRALUMINAL PROSTHESIS WITH CONNECTING SECTION

TECHNICAL FIELD

The present invention relates generally to intraluminal grafts or "stents" and, more specifically, to improved-guidewire-access modular intraluminal prostheses having a sealing section where one module attaches to another.

BACKGROUND OF THE INVENTION

A stent is an elongated device used to support an intraluminal wall. In the case of a vascular stenosis, a stent provides an unobstructed conduit for blood in the area of the stenosis. Such a stent may also have a layer of prosthetic material that covers or lines the inside or outside thereof. Such a covered or lined stent is commonly referred to in the art as an intraluminal prosthesis, an endoluminal or endovascular graft (EVG), or a stent-graft. As used herein, however, the term "stent" is a shorthand reference referring to a covered or uncovered such stent.

Such a prosthesis may be used, for example, to treat a vascular aneurysm by removing the pressure on a weakened part of an artery so as to reduce the risk of rupture. Typically, an intraluminal stent or prosthesis is implanted in a blood vessel at the site of a stenosis or aneurysm endoluininally, i.e. by so-called "minimally invasive techniques" in which the stent, restrained in a radially compressed configuration by a sheath or catheter, is delivered by a stent deployment system or "introducer" to the site where it is required. The introducer may enter the body through the patient's skin, or by a "cut down" technique in which the entry blood vessel is exposed by minor surgical means. When the introducer has been threaded into the body lumen to the stent deployment location, the introducer is manipulated to cause the stent to be released from the surrounding sheath or catheter in which it is restrained (or alternatively the surrounding sheath or catheter is retracted from the stent), whereupon the stent expands to a predetermined diameter at the deployment location, and the introducer is withdrawn. Stent expansion may be effected by spring elasticity, balloon expansion, or by the self-expansion of a thermally or stress-induced return of a memory material to a pre-conditioned expanded configuration.

Modular stents and prostheses are known in the art for in vivo assembly, particularly as applied to a bifurcated artery or vein, such as, for example, the bifurcation in the mammalian aortic artery into the common iliac arteries. The endoluminal navigation of a second component to find and mate with a previously deployed first component can be difficult.

Typically, the surgeon must navigate a guidewire to find an opening in the previously placed component, where the second component is to be mated therewith. Because of the tortuosity of the anatomy, the difficulty of visualizing that opening via fluoroscopy, and the two-dimensional nature of the fluoroscopic image, accessing that opening with the guidewire is one of the most difficult and time-consuming aspects of deploying such a prosthesis. Additionally, because of the difficulty in making the connection with that opening, the guidewire may inadvertently miss the opening and dislodge thrombus or pierce a wall of the lumen in which the prosthesis is being placed.

In a design known prior to the invention and as shown in FIG. 1, a body 30 disposed in the infrarenal area of the aorta with an integral elongated segment 32 extending into a first iliac artery 16 also comprises an integral funnel-shaped segment 34 alongside the elongated segment. Funnel-shaped segment 34 is adapted to capture guidewire 18 introduced from the iliac artery 16' into mouth 36 and to prevent the guidewire from contacting artery wall 26. The second modular component of the graft 37 is then inserted along guidewire 18 into funnel-shaped segment 34 from the iliac artery 16' and thus guided to a connection with first part body 30 at port 38. No particular type of connection between body 30 and second modular component 37 is disclosed in this prior known construction except as shown in FIG. 1.

SUMMARY OF THE INVENTION

The present invention provides an intraluminal prosthesis adapted for insertion into and assembly within a body lumen to repair the lumen. The prosthesis comprises a female mating member comprising a main body portion, a funnel-shaped end, a connecting segment connecting the main body portion to the funnel-shaped end; and a male mating member adapted for secure and/or fluid-tight assembly with the connecting segment of the female mating member. The connecting segment may be essentially cylindrical or it may taper with decreasing diameter from the main body to the funnel-shaped end. The connecting segment and adjacent funnel-shaped end may together form an hourglass-shaped end.

A biocompatible material may cover one or both of the inner mating surface of the sealing segment and the outer mating surface of the male mating member adapted for contact with the sealing segment. The biocompatible graft material may cover the inner surface of the funnel-shaped end, and in particular, may cover the outer surface of the entire prosthesis except for the funnel-shaped end, which is covered only on the inner surface thereof.

The prosthesis may be bifurcated into first and second extensions depending from the main body section, wherein one or both of the extensions comprise an integral female mating member with a connecting segment as disclosed and claimed herein. One extension may comprise an integral first leg member that depends from the main body alongside the integral female mating member extension into which the male mating member mates to comprise a second leg member. Specifically, the prosthesis may form a bifurcated aortic intraluminal prosthesis adapted for deployment in the infra-renal aorta and the iliac arteries, where the main body component forms the main aortic body, the integral first leg member forms the first iliac segment, and the second leg member forms the second iliac segment.

It is to be understood that both the foregoing general description and the following detailed description are exemplary, but are not restrictive, of the invention.

BRIEF DESCRIPTION OF DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF INVENTION

Figure 1:
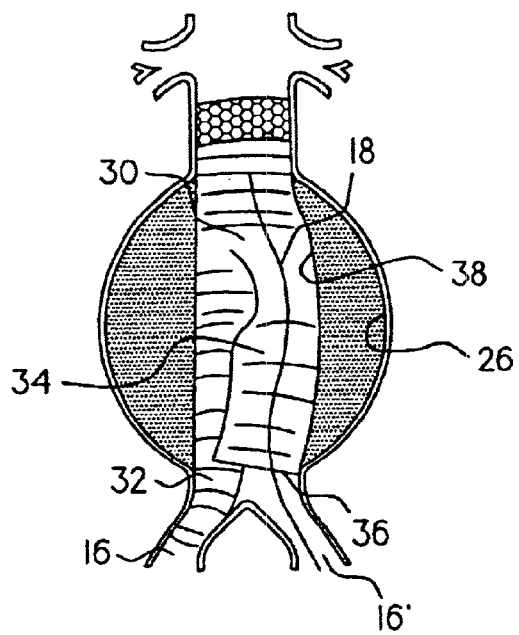
FIG. 1 is a schematic illustration of a cross-section of a bifurcated artery, showing an intraluminal prosthesis of the prior art inserted therein.

Referring now to the drawing, wherein like reference numerals refer to like elements throughout, FIGS. 2–4B are schematic illustrations of exemplary intraluminal prostheses of the present invention.

Figure 2:
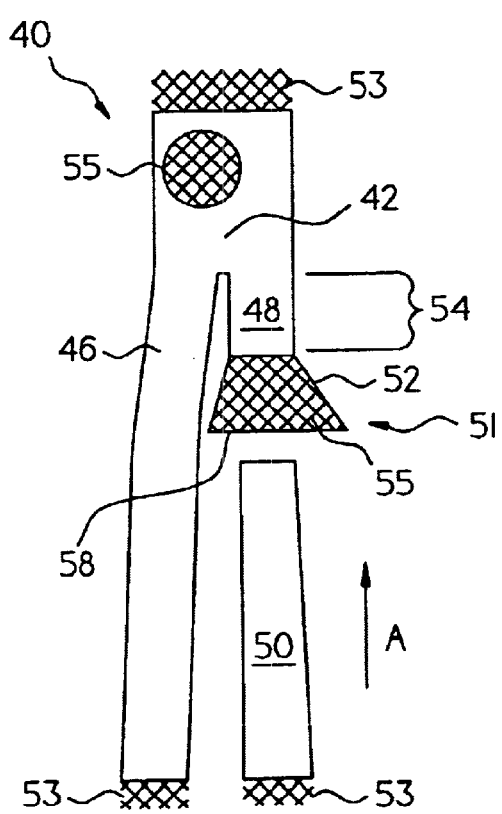
FIG. 2 is a schematic illustration of an exemplary intraluminal prosthesis of the present invention having a funnel-shaped female mating member and a generally cylindrical sealing section.
Figure 3:
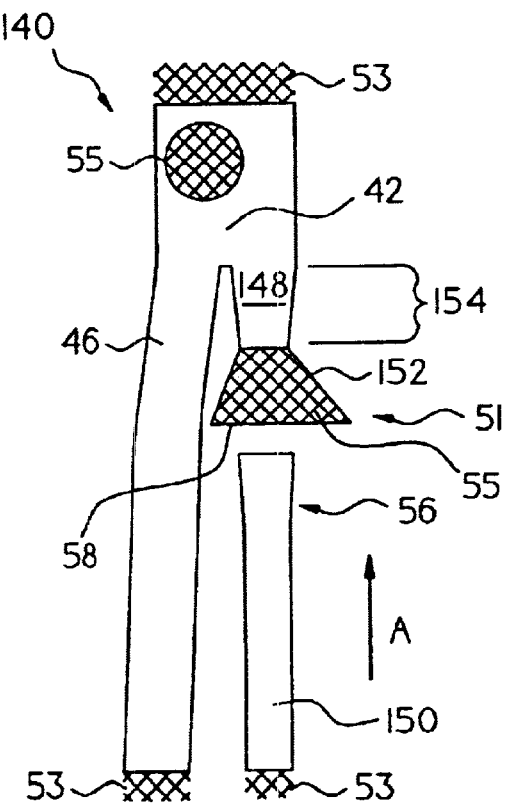
FIG. 3 is a schematic illustration of another exemplary intraluminal prosthesis of the present invention having a funnel-shaped female mating member and a tapered sealing section.

Prosthesis 40, as shown in FIG. 2, comprises a main body component 42 from which an integral first leg portion 46 and an integral female mating member 48 depend therefrom. As used herein, "distal" refers to the end farthest from the access location outside the body lumen, and "proximal" refers to the end closest to the access location outside the body lumen. Integral first leg portion 46 is adapted to extend into one branch of a bifurcated artery (such as branch 16 as shown in FIG. 1, when prosthesis 40 is mounted into a similar artery). Female mating member 48 is adapted to be positioned aligned with the other artery branch (16'). Prosthesis 40 also comprises an independent, tubular second leg portion 50 adapted for mating with female mating member 48 by insertion along the direction of arrow "A".

Female mating member 48 has a proximal end 51 comprising a funnel-shaped passage 52 adapted to help direct the guidewire into the female mating member, thereby facilitating improved guidewire access during placement of the prosthesis. Funnel-shaped passage 52 may comprise stent structure 55 mounted outside of graft material 58. Stent structure 55 may be mounted outside of graft material 58 in funnel-shaped passage 52 as shown in FIG. 2 so that the guidewire will not become entangled between the stent wires and the graft material. In another embodiment, not shown, graft material 58 may cover both the inside and outside of stent structure 55 in funnel-shaped passage 52. As shown in FIG. 2, the remainder of prosthesis 40 comprises graft material 58 on the outside of stent structure 55 (shown in circular cutaway) except for at anchoring ends 53. Anchoring ends 53 comprise sections of stent having no overlying graft material (and, preferably, no underlying graft material either), so that body tissue may grow around the stent structure of ends 53 to more permanently anchor the stent in place.

In accordance with the present invention, prosthesis 40 also comprises connecting section 54 between funnel-shaped passage 52 and main body 42. Connecting section 54 is adapted for securing second leg portion 50 into female mating member 48. As shown in FIG. 2, connecting section 54 is essentially cylindrical with the same diameter throughout. In an alternative embodiment, shown in FIG. 3, female mating member 148 of prosthesis 140 may have a connecting section 154 that has a tapered diameter decreasing between main body 42 and funnel-shaped passage 152. Second leg portion 150 may have a mating tapered section 56 adapted to mate snugly with connecting section 154. To provide a fluid-tight seal between second leg portion 50, 150 and respective connecting section 54, 154, connecting section 54, 154 may be lined inside with graft material (not shown) whereas second leg portion 50, 150 may be covered outside with graft material. In this way, the interface between second leg portion 50, 150 and respective connecting section 54, 154 provides graft-material-to-graft-material contact to effect a tight seal.

Figure 4A:
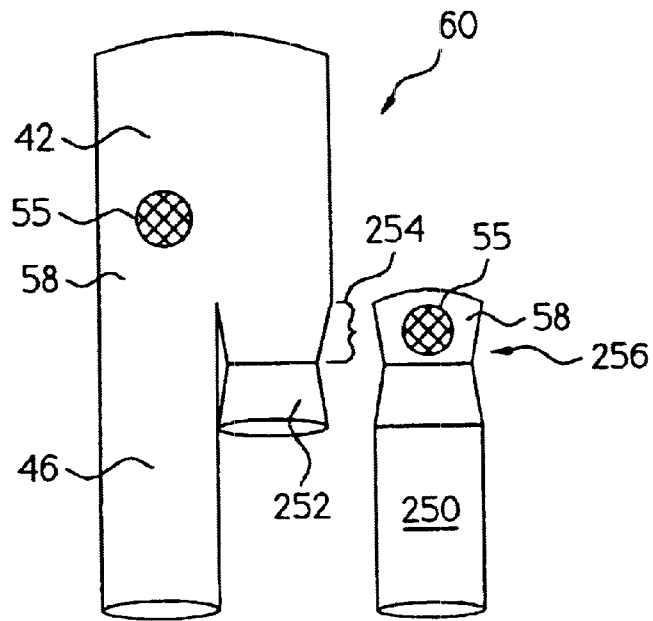
FIGS. 4A and 4B are schematic illustrations of an exemplary intraluminal graft structure of the present invention having a female mating member with an hourglass-shaped end and a male mating member having a mating hourglass-shaped end, shown in disassembled and assembled configurations, respectively.
Figure 4B:
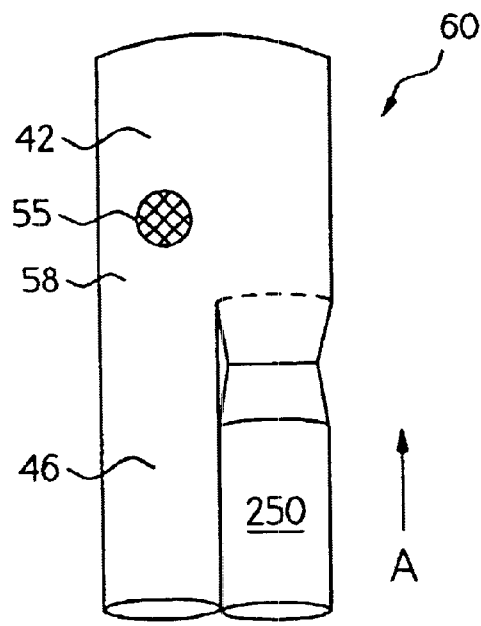

In yet another alternative embodiment, as shown in FIGS. 4A and 4B, exemplary prosthesis 60 may have a female mating member 248 with a tapered connecting section 254 and adjacent funnel-shaped passage 252 that together form an hourglass-shaped 256. Second leg portion 250 thus includes a mating hourglass-shaped end 256'. Mating hourglass-shaped ends 256 and 256' allow second leg portion 250 to be inserted into main body 42 along arrow "A" in a compressed form, expanded, and then tensionally pulled opposite arrow "A" until it locks into place as shown in FIG. 4B. The self-locking hourglass seal decreases the likelihood of placing the interlocking modular component too far into the graft, which can result in clinical problems such as inadequate sealing to the iliac, thrombosis, or stenosis in some cases.

In prosthesis 60 as shown in FIGS. 4A and 4B, similar to the other embodiments shown and described above, funnel-shaped passage 252 may comprise stent structure covered by graft material on the inside to prevent entanglement of the guidewire during navigation therein. Additionally, as shown in FIGS. 4A and 4B, funnel-shaped passage 252 may also be covered outside with graft material 58. The remainder of prosthesis 60 typically comprises stent structure 55 (shown in circular cutaway) covered outside by graft material 58. Where anchoring ends (not shown in FIGS. 4A and 4B) are present, the stent structure is typically left uncovered by graft material. To effect a fluid-tight seal, the stent structure in both funnel-shaped passage 252 and connecting section 254 may be covered on the inside by graft material (not shown) wherein second leg portion 250 comprises graft material 58 on the outside of stent structure 55 (shown in circular cutaway) so that graft-material-to-graft-material contact is provided at the interface of hourglass-shaped end 256 with funnel-shaped passage 252 and connecting section 254.

Any of the embodiments shown herein may include radiopaque markers positioned on the stent as necessary to provide "vision" via fluoroscopy to the attending surgical team. "Radiopaque marker" as used herein encompasses any discrete area of different radiopacity as compared to a surrounding area. Specifically, such markers may be advantageously placed at the mating ends of the female and male mating members to facilitate mating. In particular, with respect to the hourglass-shaped ends 256 and 256' shown in FIGS. 4A and 4B, radiopaque markers may be placed at the narrow diameter waists 257 and 257' of female mating member 248 and second leg portion 250, respectively, to facilitate proper alignment.

A prosthesis of the present invention may be constructed with any materials known in the art, and may be deployed using an introducer catheter such as those well-known known in the art. The stent material used to form a prosthesis of the present invention is preferably self-expanding, shape-memory nitinol, but may be elastically or thermally self-expanding, balloon expandable, or expandable by any method known in the art. The graft material may be any material known and used for such purposes in the art, including fluid-impermeable textiles or polymers such as polyester, polyurethane, or polytetrafluoroethylene. Although illustrated herein with respect to a bifurcated design, the funnel-shaped end and adjacent sealing section may be applied to non-bifurcated and multi-branched modular intraluminal prosthesis designs as well.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. An intraluminal modular prosthesis comprising:

a pair of tubular mating members comprising a female mating member and a male mating member adapted for in vivo assembly securely with one another, the pair of tubular mating members having an assembled configuration and a disassembled configuration;

the female mating member comprising a main body and at least one depending member having a funnel-shaped end and a connecting segment that tapers with decreasing diameter from the main body to the funnel-shaped end along a first axial length, the funnel-shaped end flaring with increasing diameter from the connecting segment along a second axial length, the connecting segment and adjacent funnel-shaped end together forming an hourglass-shaped end;

the male mating member comprising an hourglass-shaped end in both the disassembled configuration and the assembled configuration, the hourglass-shaped end in the assembled configuration comprising a tapered section adapted to contact the female mating member connecting segment and a flared section adapted to contact the female mating member funnel-shaped end all along the second axial length;

the hourglass-shaped ends of the female mating member and the male mating member adapted to self-lock with one another in the assembled configuration to form a tight seal.

2. The prosthesis of claim 1, wherein said prosthesis has a first compressed configuration for introducing said prosthesis into the body lumen, and a second expanded configuration for deployment of said prosthesis within the body lumen.

3. The prosthesis of claim 2 wherein the prosthesis is adapted to be converted from the compressed configuration to the expanded configuration by a mechanism selected from the group consisting of: balloon expansion, shape memory material self-expansion, and elastic self-expansion.

4. The prosthesis of claim 1 further comprising a biocompatible graft material covering one or both of an inner mating surface of the connecting segment and an outer mating surface of the male mating member adapted for contact with said connecting segment.

5. The prosthesis of claim 1 wherein a biocompatible graft material covers an inner surface of the funnel-shaped end.

6. The prosthesis of claim 5 wherein said biocompatible graft material also covers an inner surface of the connecting segment.

7. The prosthesis of claim 6 wherein said biocompatible graft material also covers at least a portion of the outside of said female mating member.

8. The prosthesis of claim 6 wherein an outer surface of at least a mating section of said male member is covered with said biocompatible graft material.

9. The prosthesis of claim 1 wherein a biocompatible graft material covers (a) an outer surface of all of said prosthesis except for one or more anchoring ends adapted to allow tissue growth thereabout once deployed within said body lumen and, optionally, said funnel-shaped end, and (b) an inner surface of said funnel-shaped end.

10. The prosthesis of claim 1 wherein the prosthesis is branched into at least two extensions depending from said main body section, wherein at least one of said extensions comprises an integral female mating member and said connecting segment.

11. The prosthesis of claim 10 wherein at least one of said extensions comprises an integral first leg member that depends from said bifurcation alongside said integral female mating member.

12. The prosthesis of claim 11 wherein the male mating member comprises a second leg member.

13. The prosthesis of claim 1, wherein the prosthesis comprises a bifurcated aortic intraluminal prosthesis adapted for deployment in the infra-renal aorta and the iliac arteries.

14. A bifurcated intraluminal modular prosthesis adapted for insertion into and assembly within a bifurcated body lumen to repair the lumen, said prosthesis comprising a pair of tubular mating members comprising a female mating member and a male mating member adapted for in vivo assembly securely with one another, the pair of tubular mating members having an assembled configuration and a disassembled configuration;

the female mating member comprising a main body and at least one depending member having a funnel-shaped end and a connecting segment that tapers with decreasing diameter from the main body to the funnel-shaped end along a first axial length, the funnel-shaped end flaring with increasing diameter from the connecting segment along a second axial length, the connecting segment and adjacent funnel-shaped end together forming an hourglass-shaped end, the female mating member having an outer surface covered with a biocompatible graft material except for one or more anchoring ends and, optionally, said funnel-shaped end, said funnel-shaped end having an inner mating surface covered with said biocompatible graft material;

the male mating member comprising an hourglass-shaped end in both the disassembled configuration and the assembled configuration, the hourglass-shaped end in the assembled configuration comprising a tapered section adapted to contact the female mating member connecting segment and a flared section adapted to contact the female mating member funnel-shaped end all along the second axial length, the male mating member having an outer surface covered with said biocompatible graft material;

the hourglass-shaped ends of the female mating member and the male mating member adapted to self-lock with one another in the assembled configuration to form a tight seal.

15. An intraluminal prosthesis adapted for insertion from a distal location into and assembly within a body lumen to repair the lumen in a proximal location, said prosthesis comprising a pair of tubular mating members comprising a female mating member and a male mating member adapted for in vivo assembly securely with one another, the pair of tubular mating members having an assembled configuration and a disassembled configuration;

the female mating member comprising a main body portion that branches into at least two depending members, each depending member having an external diameter, at least one of said depending members having a funnel-shaped end and having a connecting segment having a defined axial length connecting said main body portion to said funnel-shaped end, the funnel-shaped end having a diameter that increases distally in a first slope and the connecting segment having a diameter that decreases distally in a second slope, the funnel-shaped end and the connecting segment together forming a female interface for receiving the male mating member;

the male mating member comprising in both the disassembled configuration and the assembled configuration a flared section having a diameter that increases distally and a tapered section having a diameter that decreases distally, the flared section and the tapered section together forming a male interface for connection with the female interface, the flared section in the assembled configuration adapted to contact the female mating member funnel shaped end and having the first slope and the tapered section in the assembled configuration adapted to contact the female mating member connecting segment and having the second slope;

the female interface and the male interface adapted to self-lock with one another in the assembled configuration to form a tight seal.

16. The intraluminal prosthesis of claim 15, wherein the prosthesis is a bifurcated prosthesis adapted for insertion into and assembly within a bifurcated body lumen to repair the lumen;

said female mating member having an outer surface covered with a biocompatible graft material except for one or more anchoring ends and, optionally, said funnel-shaped end, said funnel-shaped end having an inner mating surface covered with said biocompatible graft material; and said male mating member having an outer surface covered with said biocompatible graft material.

* * * * *